United States Patent [19]

Bellotti et al.

[11] Patent Number: 4,457,749
[45] Date of Patent: Jul. 3, 1984

[54] SHIELD FOR CONNECTORS

[75] Inventors: Marc Bellotti, Winnetka; Robert Flagler, Libertyville, both Ill.

[73] Assignee: Baxter Travenol Laboratories, Inc., Deerfield, Ill.

[21] Appl. No.: 369,709

[22] Filed: Apr. 19, 1982

[51] Int. Cl.³ ............................................. A61M 5/14
[52] U.S. Cl. .................................... 604/29; 604/244; 604/411; 604/905
[58] Field of Search ................ 604/29, 244, 408–414, 604/905, 283, 48, 180; 403/23, 50, 51; 285/3, DIG. 24, 45, 423

[56] References Cited

U.S. PATENT DOCUMENTS

| 2,452,643 | 11/1948 | Fields | 604/905 X |
| 2,941,532 | 6/1960 | Borin | 604/48 |
| 3,106,415 | 10/1963 | Breunich | 285/45 X |
| 3,537,457 | 11/1970 | Heimlich | 604/48 |
| 3,826,261 | 7/1974 | Killinger | 604/414 X |
| 3,837,685 | 9/1974 | Miller | 285/45 |
| 3,986,508 | 10/1976 | Barrington | 604/905 |
| 3,993,063 | 11/1976 | Larrabee | 604/414 X |
| 4,056,116 | 11/1977 | Carter et al. | 604/905 X |
| 4,114,626 | 9/1978 | Beran | 604/180 X |
| 4,157,723 | 6/1979 | Granzow et al. | 604/244 X |
| 4,195,632 | 4/1980 | Parker et al. | 604/905 X |
| 4,201,208 | 5/1980 | Cambio, Jr. | 604/411 |
| 4,203,443 | 5/1980 | Genese | 604/413 |
| 4,323,065 | 4/1982 | Kling | 604/283 |
| 4,340,052 | 7/1982 | Dennehey et al. | 604/905 X |
| 4,346,703 | 8/1982 | Dennehey et al. | 604/29 |
| 4,354,490 | 10/1982 | Rogers | 604/905 X |
| 4,392,853 | 7/1983 | Muto | 604/180 X |

FOREIGN PATENT DOCUMENTS 2853635 6/1980 Fed. Rep. of Germany .
A090275 11/1967 France ................................ 604/244

OTHER PUBLICATIONS

Sherer, M. D. "Sterile Coupling Device for Deglycerolizing Red Blood Cells", Dhew Pub. #(NIH)-76-1004, Mar. 14, 1975, pp. 43-51.

Primary Examiner—C. Fred Rosenbaum
Assistant Examiner—Michelle N. Lester
Attorney, Agent, or Firm—Paul C. Flattery; Garrettson Ellis

[57] ABSTRACT

In a fluid flow set defining connector means at one end of a length of tubing for forming a sealed essentially aseptic connection with the second connector to permit fluid transfer through the joined connectors. The improvement of a flexible, tubular shield member threaded about the length of tubing in telescoping relation and movable along its length for shielding the connection.

14 Claims, 4 Drawing Figures

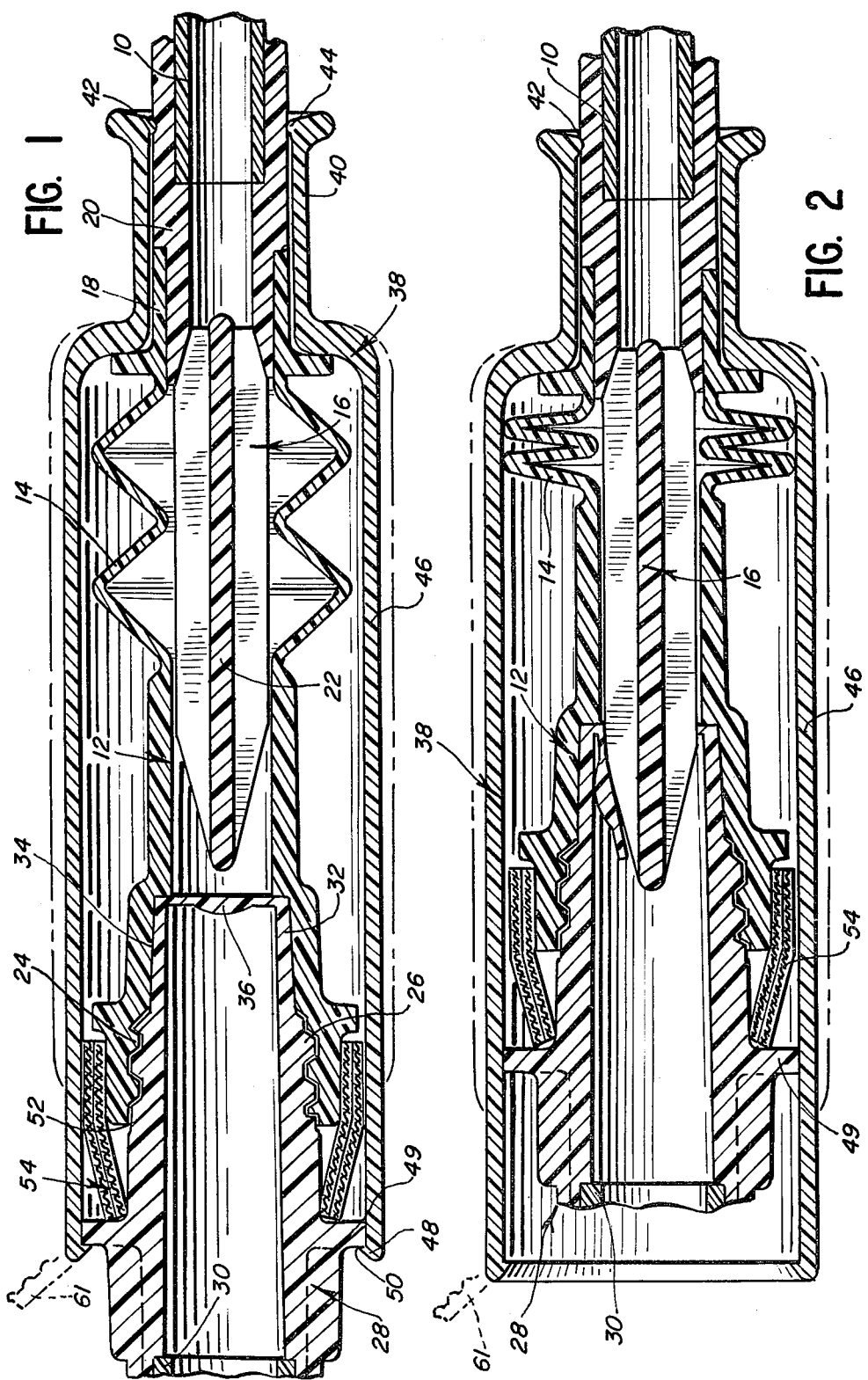

SHIELD FOR CONNECTORS

BACKGROUND OF THE INVENTION

In U.S. patent application Ser. No. 329,163, filed Dec. 10, 1981, an ultraviolet sterilizable connector having a spike with projecting vanes is disclosed. This and various other structures known to the art have been proposed as a means for providing essentially aseptic connection between two tubing ends, the connection being initially made and then irradiated with ultraviolet radiation which passes through the ultraviolet transparent material of the connector to sterilize its interior.

Such a connection system may be used in peritoneal dialysis, for example the presently practiced procedure of continuous ambulatory peritoneal dialysis (CAPD), or in any other operation where it is very important to maximize the probability that the connection made is sterile. Dialysis solution then passes through the connection to and from the peritoneal cavity, with a reduced risk of peritonitis because an essentially sterile connection has been made.

It has been found to be desirable for the connection between the two conduits to be provided with further protection, particularly in the event where the patient carries the flattened, peritoneal dialysis solution bag and the joined connection on his person throughout the day between exchanges of dialysis solution, as is a common practice of CAPD. Previously, this has been accomplished by a gauze wrap, or by the use of a so-called "clam shell" connector as disclosed, for example, in U.S. Application Ser. No. 194,733 filed Oct. 7, 1980 now U.S. Pat. No. 4,340,052. The clam shell connector comprises a pair of housing halves made of a single piece of plastic joined together by an integral plastic hinge and typically containing absorbent pads which carry an antiseptic such as povidone iodine to bathe the exterior of the connection in such antiseptic while it is carried within the clam shell connector.

However, especially in connection systems which are intended for ultraviolet irradiation, the wrap or the clam shell connector must be removed by opening and placed somewhere in a separate location during the ultraviolet irradiation, because even if the wrap or clam shell connector were made of an ultraviolet transmissive material, there would be a significant loss in ultraviolet intensity if one attempted to irradiate the connection through the wrap or clam shell connector.

In accordance with this invention, a shield design for a connection is provided in which the shield design can be slipped away from the connection for ultraviolet irradiation, or for making or breaking the connection, but it is easily retained as a part of the system without being a separate part, subject to loss. It is easily placed into protecting relation around the connection site as desired. Furthermore, the joined connectors can be reconnected, adjusted, or disconnected, if desired, without the displacement of the shield member of this invention so that the shield member can continue to provide some protection to the connectors as they are opened and closed. Also, in this manner the shield member can enclose a wrapped antiseptic band surrounding the connectors to reduce the possibility of spilling of the antiseptic (which is a highly colored and staining material when povidone iodine is used) so that the staining of the fingers or the furniture on which the patient is sitting during the operation is reduced.

However, the tubular shield of this invention may be readily removed, sliding up the tubing, for exposure of the connection when ultraviolet irradiation or other antibacterial treatment of the connection junction is desired. Following the irradiation, the tubular shield member can slide back into protecting relation with the connecting junction of the joined connectors.

DESCRIPTION OF THE INVENTION

In accordance with this invention, a fluid flow set defining connector means on one end of a length of tubing for forming a sealed, essentially aseptic connection with a second connector is provided, to permit fluid transfer through the joined connectors.

By this invention, a flexible, tubular shield member is disposed about the length of tubing in telescoping relation and movable along its length. One end of the shield member defines a first aperture to which the length of tubing extends, the first aperture being proportioned to define a first seal with the length of tubing. The other end of the flexible tubular shield defines a second aperture large enough to receive the connector means into the interior of the tubular shield member. As the result of this, the connection junction between the connector means and a second connector can be protected, while at the same time the connector means may be manually gripped by gripping the flexible tubular shield member for the purpose of facilitating connection or disconnection of the connector means from a second connector.

The connector means can be joined to a second connector, with both connectors being positioned within the bore of the shield member. The second connector may define an annular flange that defines a sliding second seal with the bore of the shield member so that the junction between the two connectors is protected in sealed relation at both ends of the tubular shield member.

Typically the connector means and second connector are radially spaced from the shield member, except for the sliding second seal which is provided by the annular flange. The connector means in the second connector are preferably joined together in screw thread relationship, but, alternatively or additionally, the connector means and second connector may be joined together in the relationship of a penetrating spike passing through a diaphragm and sealed port.

Preferably, the connector means and second connector may be threaded together in screw thread relationship, followed by an ultraviolet irradiation step. Thereafter, the penetrating spike may be manipulated to pass through the diaphragm to open flow between the two connectors and the tubes upon which they are carried, permitting the transfer of peritoneal dialysis solution between the patient's peritoneal cavity and a supply container.

It also desirable for the junction of the connector means of the second connector to be wrapped in a coiled strip of Velcro-type fabric, which is a well known material, locked together in overlapping, coiled ends. The strip carries on its inner, coiled surface a porous pad soaked in antiseptic surrounding the junction, to provide the desired continuous sterilization of the junction area.

It may also be desirable for the shield member to define convolutions. This permits the axial expansion and collapse of the shield member to correspondingly permit axial relative motion between the connectors of the second connector, particularly for the purpose of permitting the spike of one of the connector means or second connector to penetrate a diaphragm on the other of the connector means or second connector without any sliding seal motion between the shield member and the structure enclosed therein.

DESCRIPTION OF THE DRAWINGS

FIG. 1 is a longitudinal sectional view of connector means on the end of a length of tubing in connected relation with a second connector, the junction between the connector means and second connector being surrounded and enclosed with a flexible tubular shield in accordance with this invention.

FIG. 2 is a longitudinal sectional view similar to FIG. 1 in which the spike of the connector means is shown to be advanced to penetrate the diaphragm carried by the second connector.

DESCRIPTION OF SPECIFIC EMBODIMENTS

Figure 3:
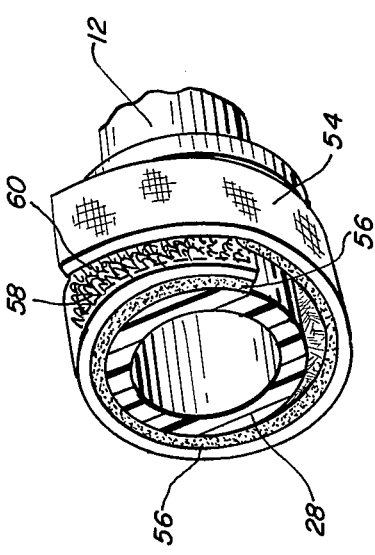
FIG. 3 is a fragmentary, enlarged perspective view showing details of the coiled strip of Velcro-type fabric which is locked together in overlapping ends and surrounding the junction of the connector means and second connector.

Referring to the drawings, FIG. 1 shows a length of tubing 10 which may be part of a set for connection in conventional manner to a Tenckoff catheter or the like implanted in communication with the peritoneal cavity of a patient. Carried on the end of length of tubing 10 is a connector means or first connector 12 comprising a hollow tubular member in flow communication with tube 10, and made of an ultraviolet transparent material, being specifically of a design as disclosed in the previously cited application Ser. No. 329,163, being made for example of a polyolefin material or Surlyn, sold by the DuPont Chemical Co. A portion of the tubular connector means 12 may comprise bellows member 14, which permits connector member 12 to be advanceable and retractable relative to spike 16, which carries tubular connector 12 at its end 18 in sealed manner and defines a tubular portion 20, which is an integral part of spike 16. Spike 16, in turn, is sealed at the end of tube 10. The forward portion of spike 16, as shown, is defined by a plurality of radial vanes 22 with liquid flow channels being defined between vanes 22.

The forward portion of tubular connector means 12 defines internal screw threads 24 which are proportioned to receive the external screw threads 26 of a second connector 28. Second connector 28, in turn, may be carried on the end of flexible tubing 30, being solvent sealed in place or otherwise adhered, and may communicate with an otherwise conventional container of peritoneal dialysis solution, particularly a collapsible bag.

Second connector 28 defines a luer connector portion 32 at a position forward of its screw threads 26, tapering in a manner to be sealingly received in luer socket 34 of connector member 12. Second connector 28 also defines a pierceable diaphragm 36 at its forward end which is capable of being punctured by spike 16.

After the two connectors have been brought together in screw-threaded relationship, with a seal being provided between projecting luer member 32 and luer socket 34, the connection may then be exposed to ultraviolet light. Spike 16 may then be relatively advanced by collapsing bellows 14 so that the spike penetrates diaphragm 36, permitting fluid flow communication between tubes 10 and 30, as shown in FIG. 2.

Connector 12 may be made of an ultraviolet transparent material so that the junction between members 32, 34, the exterior surface of diaphragm 36, and vanes 22 of spike 16 may all be so irradiated for antibacterial effect prior to the spike penetrating diaphragm 36, as described in the previously cited patent application.

In accordance with this invention, a flexible tubular shield 38 is provided, which is preferably made of a transparent plastic material, for example oriented polypropylene, polyethylene or the like. As shown, tubular shield 38 is threaded about the length of tubing 10 (including connector member 12) in telescoping relation, and is movable along its length. The rear end 40 of shield member 38 defines a first aperture 42 which is proportioned to define a first seal at annular, inwardly projecting flange 44 which, of course, includes the tubular rear portion 20 of spike 16 as shown. Thus, as desired, shield 38 may be retracted away from connectors 12, 28 by sliding along tubing 10 when desired, i.e., for connecting the two connectors 12, 28 and during the ultraviolet irradiation step. Thereafter, shield member 38 may be brought into surrounding relationship with the junction between the two connectors again.

Tubular shield 38 also defines an enlarged, tubular segment 46 and annular detent member 48 on its other end, which other end defines second aperture 50 which is large enough to receive the two connectors 12, 28 into the interior of tubular shield 38. Because of the flexibility of tubular shield 38, either or both of connectors 12, 28 can be manually gripped by gripping the flexible tubular shield member while enclosed therein. Detent member 48 resists accidental disconnection of the connectors.

Annular flange 49 of second connector 28 may be proportioned to provide a sliding seal with the interior surface of enlarged tubular portion 46 of shield member 38 so that a seal is maintained as the connectors are brought together by the advancement of spike 16 as in FIG. 2. In this instance, annular seal ridge 42 can remain stationary in sealing relation with member 20, while flange 49 slides in the manner indicated in FIGS. 1 and 2.

The outer entrance 52 to the junction between connectors 12, 28 may be wrapped with a coiled strip of Velcro-type fabric 54 which is locked together at overlapping, coiled ends, the strip carrying on its inner coiled surface a porous pad 56 which may be soaked in povidone iodine as shown in FIG. 3. The term "Velcro" is a trademark for a patented and commercially available material which is utilized in a wide variety of uses. The fabric comprises a large array of hooks on one side of the fabric and loops on the other side of the fabric, which lock together when the two sides of fabric are pushed into joining contact. As shown here, the loops 58 on one side of fabric 54 may lock with a small number of hooks 60 which occupy part of strip 54 in the same plane as pad 56. Thus strip 54 may be easily applied to the junction between the respective connectors as shown, while shield member 38 is longitudinally removed to a displaced position along tubing 10, after the two connectors 12, 28 have been brought together and exposed if desired to ultraviolet radiation. Thereafter, shield member 38 may be placed again into its position as shown in FIG. 1, and spike 16 may be advanced as shown in FIG. 2 to open the connection.

When it is desired to make a disconnection, it may not be necessary to axially displace shield member 38, since the shield member is flexible. One can simply grip connector means 12 and rotate it relative to connector member 28, then withdrawing the connector in such circumstances as when such a manipulation is desired.

Tubing 10 is typically clamped closed in a conventional manner during the making and breaking steps between the two connectors 12, 28.

If desired, a molded tab member 61 may be provided for gripping of the shield member and longitudinally pulling it.

Figure 4:
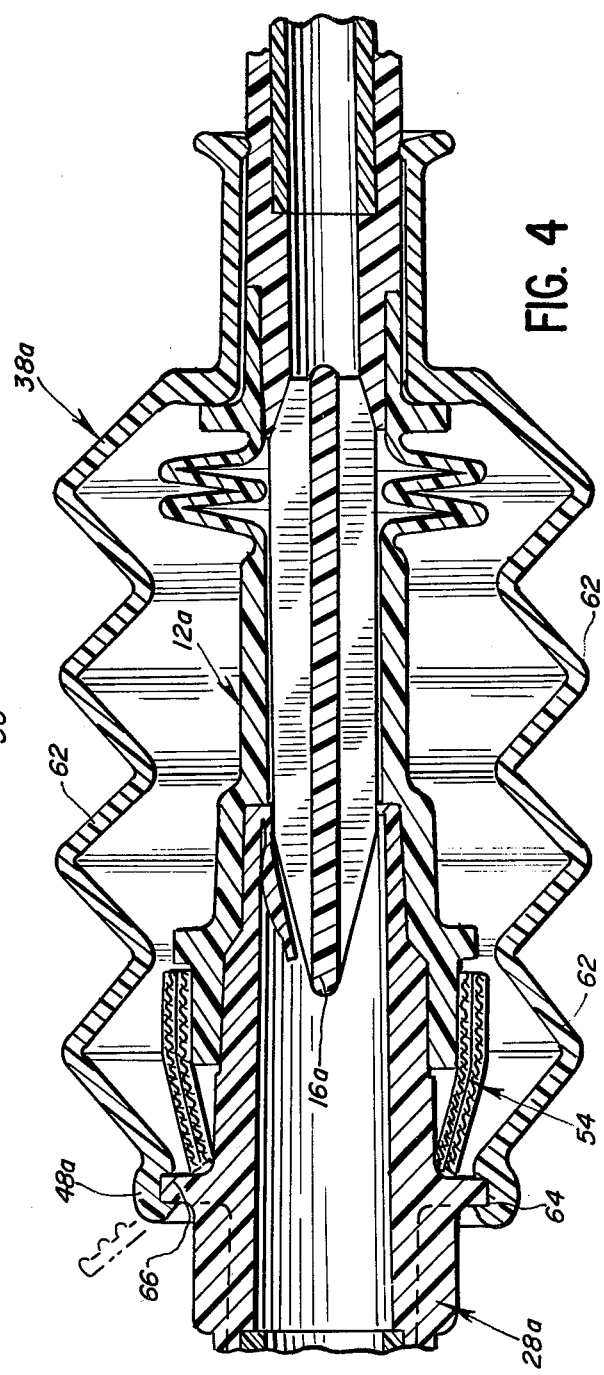
FIG. 4 is a longitudinal sectional view of an alternative embodiment of the structure of this invention.

Turning to FIG. 4, another embodiment of this invention is disclosed. Connectors 12a and 28a may be of identical design to the previous embodiment and may carry the coiled strip 54 of Velcro-type fabric if desired.

In this embodiment, tubular shield member 38a may be of broadly similar design to that of shield member 38, except that member 38a carries a series of convolutions 62.

As one difference in the embodiment, the screw thread connection between connectors 12a and 28a is optionally omitted, the connectors being held together by a frictional seal in the area where spike 16a penetrates into connectors 28a. Also, annular detent member 48a may be modified in this embodiment to define annular groove 64 which can receive flange 66 of connector 28a. Accordingly, as spike member 16a is advanced after connection between connectors 12a, 28a, instead of a sliding seal as in the previous embodiment, shield member 38a collapses longitudinally by flexing of the convolutions 62 so that a positive seal is provided rather than a sliding seal at flange 66.

The above has been offered for illustrative purposes only, and is not intended to limit the scope of the invention of this application, which is as defined in the claims below.

That which is claimed is:

1. In a fluid flow set defining connector means on one end of a length of tubing for forming a sealed, essentially aseptic connection with a second connector, to permit fluid transfer through the joined connectors, the improvement comprising, in combination:
a tubular shield member disposed about said length of tubing in telescoping relation and movable along its length, one end of said shield member defining a first aperture through which the length of tubing extends, said first aperture being defined by a reduced diameter section and proportioned to define a first seal with the length of tubing, the other end of said tubular shield defining a second aperture large enough to receive said connector means into the interior of the tubular shield member, said connector means being joined to a second connector, both connectors being positioned within the bore of said shield member, said second connector defining an annular flange that defines a sliding second seal with the bore of the shield member.

2. The fluid flow set of claim 1 in which said connector means and second connector are spaced from the shield member, except for the sliding second seal with the annular flange.

3. The fluid flow set of claim 1 in which said connector means and second connector are joined together in screw thread relationship.

4. The fluid flow set of claim 1 in which said connector means and second connector are joined together in the relationship of a penetrating spike passing through a diaphragm of a sealed port.

5. The fluid flow set of claim 1 in which the junction of the connector means and second connector is wrapped in a coiled strip of Velcro-type fabric, locked together at overlapping, coiled ends, said strip carrying on its inner, coiled surface a porous pad soaked in antiseptic surrounding said junction.

6. The fluid flow set of claim 1 in which said tubular shield member is transparent and flexible.

7. The fluid flow set of claim 1 which is for transferring liquids between a supply container and the peritoneal cavity of a patient.

8. The fluid flow set of claim 1 in which said first seal is a sliding seal.

9. The fluid flow set of claim 1 in which said shield member further defines convolutions to permit axial expansion and collapse to correspondingly permit axial relative motion between the connector means and second connector.

10. In a fluid flow set defining connector means on one end of a length of tubing for forming a sealed, essentially aseptic connection with a second connector, to permit fluid transfer through the joined connectors, the improvement comprising, in combination:
a tubular shield member disposed about said length of tubing in telescoping relationship and movable along its length, one end of said shield member defining a first aperture through which the length of tubing extends, said first aperture defined by a reduced diameter section and proportioned to define a first sliding seal with the length of tubing, the other end of said tubular shield defining a second aperture large enough to receive said connector means into the interior of the tubular shield, said connector means being joined to a second connector, both connectors being positioned within the bore of said shield member, said second connector defining an annular flange that defines a sliding second seal with the bore of the shield member said connector means defining screw threads for a sealing connection with the second connector.

11. In a fluid flow set defining connector means on one end of the length of tubing forming a sealed, essentially aseptic connection with a second connector, to permit fluid transfer through the joined connectors, the improvement comprising, in combination:
a tubular shield member disposed about said length of tubing in telescoping relation and movable along its length, one end of said shield member defining a first aperture through which the length of tubing extends, said first aperture being defined by a reduced diameter section and proportioned to define a sliding seal with the length of tubing, the other end of said flexible tubular shield defining a second aperture large enough to receive said connector means into the interior of said tubular shield, said connector means being joined to said second connector, both connectors being positioned within the bore of said shield member, said second connector defining an annular flange that defines a sliding second seal with a bore of the shield member said connector means defining a penetrating spike for penetrating a diaphragm of a sealed port of said second connector.

12. In a fluid flow set defining connector means on one end of a length of tubing for forming a sealed, essentially aseptic connection with a second connector, to permit fluid transfer through the joined connectors, the improvement comprising, in combination:

a flexible tubular shield member disposed about said length of tubing in telescoping relation and movable along its length, the ends of said shield member defining apertures permitting said length of tubing to pass therethrough, one of said apertures being large enough to receive said connector means into the interior of the tubular shield member, and the other of said apertures being smaller to sealingly grip said tubing, said connector means being joined to a second connector, both connectors being positioned within the bore of said shield member, said second connector defining an annular flange that defines a sliding second seal with the bore of the shield member, whereby said connector means may be manually gripped by gripping said flexible tubular shield member.

13. In a fluid flow set defining connector means at one end of a length of tubing for forming a sealed, essentially aseptic connection with a second connector, to permit fluid transfer through the joined connector, the improvement comprising, in combination:

a coiled strip of fabric locked together at overlapping coiled ends positioned around the junction of said sealed, essentially aseptic connection between the connector means and second connector, said strip carrying on its inner, coiled surface a porous pad soaked in antiseptic surrounding said junction, and a tubular shield member disposed about said length of tubing in telescoping relation and movable along its length, the ends of said shield member defining apertures permitting said length of tubing to pass therethrough, at least one of said apertures being large enough to receive said connector means into the interior of the tubular shield and the other of said apertures being smaller to sealingly grip said tubing with a first sliding seal, said connector means being joined to a second connector, both connectors being positioned within the bore of said shield member, said second connector defining an annular flange that defines a sliding second seal with the bore of the shield member.

14. The fluid flow set of claim 13 in which said tubular shield member defines convolutions to permit axial collapse and expansion in a manner corresponding to axial motion between the connector means and second connector.

* * * * *